(12) United States Patent
Largent

(10) Patent No.: US 6,532,072 B1
(45) Date of Patent: Mar. 11, 2003

(54) FIBER-AMPLIFIER CAVITY FOR CAVITY RING DOWN SPECTROSCOPY

(75) Inventor: Craig C. Largent, Centerville, OH (US)

(73) Assignee: The United States of America as represented by the Secretary of the Air Force, Washinton, DC (US)

(*) Notice: Subject to any disclaimer, the term of this patent is extended or adjusted under 35 U.S.C. 154(b) by 0 days.

(21) Appl. No.: 09/523,987

(22) Filed: Mar. 13, 2000

(51) Int. Cl.[7] ............................................. G01N 21/00
(52) U.S. Cl. ..................................... 356/440; 356/339
(58) Field of Search ............................... 356/440, 437, 356/439; 385/37, 55, 50, 71

(56) References Cited

U.S. PATENT DOCUMENTS

| | | | |
|---|---|---|---|
| 5,528,040 A | 6/1996 | Lehmann | 250/343 |
| 5,815,277 A | 9/1998 | Zare et al. | 356/440 |
| 5,903,348 A | 5/1999 | Melman et al. | 356/344 |
| 5,903,358 A | 5/1999 | Zare et al. | 356/437 |
| 5,912,740 A | 6/1999 | Zare et al. | 356/437 |
| 5,986,768 A | * 11/1999 | Pipino | 356/440 |
| 6,094,267 A | * 7/2000 | Levenson et al. | 356/349 |

* cited by examiner

*Primary Examiner*—Frank G. Font
*Assistant Examiner*—Layla Lauchman
(74) *Attorney, Agent, or Firm*—Gina S. Tollefson; Gerald B. Hollins; Thomas L. Kundert

(57) ABSTRACT

A cavity ring-down spectroscopy device and method suitable for materials with low and high absorption coefficients. An optical signal introduced into an optical cavity resonates through a length of fiber amplifier coupled to the optical cavity. The optical signal resonates through a fiber amplifier active section resulting in a gain compensating for optical losses. The gain obtained by use of the fiber amplifier is then modulated between two predetermined levels. By virtue of employing an optical fiber, the cavity ring down spectroscopy device and method is insensitive to misalignment and therefore iminently capable of portability.

19 Claims, 2 Drawing Sheets

FIBER-AMPLIFIER CAVITY FOR CAVITY RING DOWN SPECTROSCOPY

RIGHTS OF THE GOVERNMENT

The invention described herein may be manufactured and used by or for the government of the United States for all governmental purposes without the payment of any royalty.

BACKGROUND OF THE INVENTION

The field of the invention is cavity ring down spectroscopy and more specifically cavity ring down spectroscopy for strongly absorbing species.

Cavity Ring Down Spectroscopy (CRDS) is a laser absorption spectroscopy technique used to measure absolute concentrations of absorbing species. In a conventional CRDS system, a sample chamber containing an absorbing material is placed in an optical resonator consisting of two spherical mirrors facing each other along a common optical axis. Light incident on and passing through one mirror circulates back and forth multiple times in the resonator, setting up standing waves having periodic spatial variations. Light exiting through the other mirror is measured to determine the light intensity present in the cavity FIG. 1 shows a prior art CRDS system. The sample absorbing material is placed in chamber 102 and two spherical mirrors facing each other are shown at 100 and 104, with the entire system stabilized on an optical table, partially shown at 101 in FIG. 1. An optical signal such as a laser beam 106 is introduced by laser 103 into the ultra-low-loss cavity and then turned off. The light introduced through mirror 104 circulates back and forth multiple times between mirrors 104 and 100. As the light oscillates inside the cavity, a small fraction is transmitted out of the cavity at each mirror. The optical photodetector shown at 105 measures the light intensity exiting the cavity. The intensity of this light exiting the cavity decays exponentially in time at a rate dependent on the total cavity losses. These losses comprise the loss from the finite reflectivity of the mirrors, from diffraction, and from any absorption within the cavity. The radiant energy stored in the resonator decreases in time, a process referred to as "ring down."

A graphical representation of this ring down phenomena is shown in FIG. 2. In FIG. 2, light intensity is represented on the y-axis at 200 and time is represented on the x-axis at 201. The decay of light intensity due to sample species absorption is shown by the curve at 202. The exponential decay of the light intensity is mathematically defined as $I(t)=e^{-t/\tau}$, where $\tau$ is the time constant that characterizes the exponential decay.

For an empty cavity that does not contain an absorbing sample, the stored radiant energy follows an exponential decay characterized by a ring down time constant that depends only on the reflectivity of the mirrors and the speed of light in the resonator. When a sample is placed in the resonator the ring down is accelerated and ideally, the intracavity energy decays almost perfectly exponentially. It can be shown that comparison of the decay time constants measured for an empty cavity and one in which absorbing species are present can be used to quantitatively determine the absolute concentration of absorbing species present in the cavity (at the given input wavelength). An absorption spectrum for the sample is obtained by plotting the reciprocal of the ring down time constant versus the wavelength of incident light. These measurements, when combined with sample specific information, are used to determine the absolute concentration of the absorbing species.

It should be noted that the sample material concentration information is contained in the ring down decay time and not the initial intensity of the laser light. Therefore, this technique is insensitive to intensity variations in the input laser. This fact enables CRDS to produce absolute concentration measurements and sets CRDS apart from competing absorption spectroscopy techniques, which can only provide data on relative concentrations. Additionally, CRDS can measure ultra-low concentrations of absorbing species (less than 1 part per billion).

CRDS has been used to characterize a variety of gas environments and in thin films deposition through evanescent coupling of the optical wave inside a totally internally reflecting prism. CRDS has also been used for measuring the concentration of contaminants in pollution control systems.

Currently, CRDS requires the total round trip losses of the cavity to be small (much less than a fraction of a percent) if useful ring down time constants are to be obtained. Therefore, the technique is currently limited to the characterization of samples (typically gas phase species) with low absorption coefficients. This precludes the characterization of liquids and solids using CRDS, as their high absorption coefficients and significant background losses result in ring down times too short to measure.

The present invention provides an improved capability cavity ring down spectroscopy (CRDS) system and makes the CRDS techniques applicable for samples with high absorption coefficients. The present invention uses the optical gain available in a fiber amplifier to compensate for all system optical losses commonly seen in conventional CRDS systems, plus those due to fiber coupling and light detection. Additionally the present invention provides a CRDS system that is immune to cavity misalignment and therefore eminently capable of portability.

SUMMARY OF THE INVENTION

The present invention provides a cavity ring-down spectroscopy device and method suitable for materials with low and high absorption coefficients. An optical signal introduced into an optical cavity resonates through a length of optical fiber coupled to the optical cavity. The optical signal resonates through a fiber amplifier active section resulting in a gain, which compensates for system optical losses. The gain obtained by use of the fiber amplifier is then modulated between two predetermined levels. By virtue of employing a fiber amplifier and avoiding the alignment sensitivity of optical mirrors, the cavity ring down spectroscopy device and method of the present invention are insensitive to misalignment and therefore capable of portability.

It is therefore an object of the invention to provide a cavity ring down spectroscopy system with the ability to measure absolute concentrations of absorbing samples characterized by significant losses, such as liquid or solids.

It is another object of the invention to provide a cavity ring down spectroscopy system insensitive to optical misalignment.

It is another object of the invention to provide a cavity ring down spectroscopy system and method where light resonates through a length of fiber amplifier coupled to an optical cavity.

It is another object of the invention to provide a cavity ring down spectroscopy system and method where light resonates through a length of fiber amplifier coupled to an optical cavity resulting in minimal loss.

DETAILED DESCRIPTION OF THE INVENTION

The present invention provides a cavity ring down spectroscopy device and method suitable for materials with low and high absorption coefficients. In contrast to the conventional practice of resonating an optical signal between two mirrors located at either end of an optical cavity, the present invention couples a length of optical fiber to either end of the optical cavity. The optical signal resonates through a fiber amplifier active section within the length of optical fiber, resulting in a gain which compensates for optical losses such as those associated with absorbing species having high background absorption coefficients, optical coupling losses, fiber coupling losses and beam splitter losses.

Figure 3:
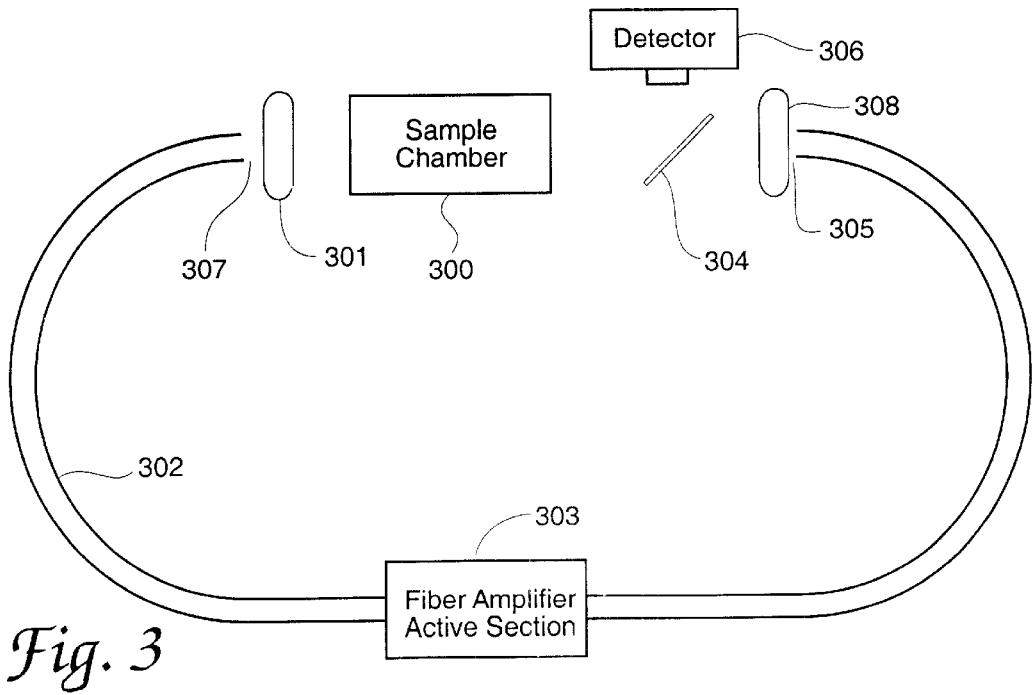
FIG. 3 shows a schematic diagram of a CRDS system using a fiber amplifier according to the invention.

FIG. 3 shows a schematic diagram of a fiber amplifier cavity spectroscopy arrangement for cavity ring down spectroscopy according to the invention. An absorbing species sample chamber is shown at 300 and an optical photodetector is shown at 306. A length of optical fiber is shown at 302 with two separate ends of the optical fiber coupled to the absorbing species sample chamber shown at 305 and 307. A fiber 303 amplifier active section 303 is shown within the length of optical fiber 302.

Figure 1:
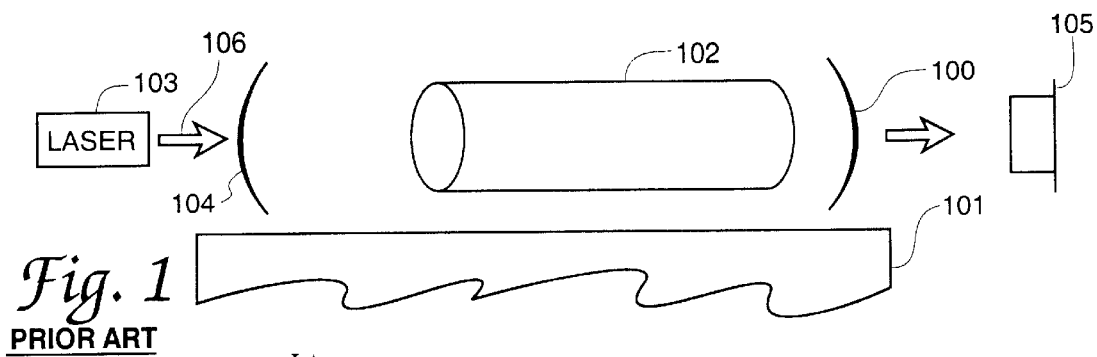
FIG. 1 shows a prior art cavity ring down spectroscopy system.
Figure 2:
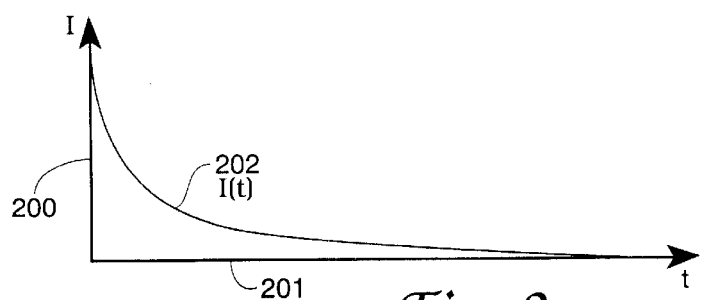
FIG. 2 shows a graphical representation of the cavity ring down phenomenon as a function of light intensity versus time.

In operation, a narrow bandwidth optical signal source is generated in the active optical fiber and sends a beam or optical signal to the sample chamber 300. In conventional systems as shown in FIG. 1, an optical signal source such as a laser shown at 103 is autonomous and is outside the optical cavity and outside the path of optical resonance. However, in the present invention the optical signal may be generated from the fiber amplifier active section, 303 in FIG. 3. Although the fiber amplifier active section provides optical gain to compensate for optical losses, it may also act as the initial optical signal source, thereby eliminating the need for an outside optical signal source and also eliminating optical loss due to the coupling of the optical signal source to the optical cavity or sample chamber. A feedback system could be employed with the arrangement of the invention to calibrate the wavelength of the laser light injected into the system to initiate operation of the system.

Generally, the absorbing species sample chamber is a cylindrical shaped compartment. However, any shaped compartment may be used, especially with the present arrangement where coupling with concave mirrors is not a consideration. The chamber 300 contains an absorbing species, a mixture of gases relative to the specific application. Each gas absorbs light at a certain level as a function of wavelength. So, the rate of light absorption for a specific gas can be associated with a specific absorption coefficient.

Referring again to FIG. 3, an optical signal is coupled to the optical cavity 300 and a portion of the optical signal is absorbed by the absorbing species gases. The degree of absorption depends on the wavelength of the optical signal and the concentration of constituent gases. The remainder of the optical signal exits the sample chamber 300 and is split by a beam splitter 304. The beam splitter 304 directs a small portion of the optical signal to a photodetector 306. The detector 306 measures the optical power present in the optical cavity 300 as a function of time.

In addition to the sample absorption losses, the system experiences optical losses due to the fiber coupling, the coupling optics and the beam splitter. A significant aspect of the invention is compensating for such losses by transmitting the signal through an optical amplifier producing gain. After the optical signal is amplified in the fiber amplifier active section 303, the optical signal is again transmitted into the absorbing species sample chamber where a portion is absorbed. The remaining optical signal then travels through the length of fiber amplifier and through the fiber amplifier active section where a gain is realized equal to the system losses. The optical signal then repeats this cycle as the optical signal "rings down" in intensity.

The ends of the optical fiber shown at 305 and 307 may have an antireflective coating to minimize loss when the optical signal is coupled to the optical fiber. Additionally, the length of optical fiber used for the CRDS cavity may be either a multimode or single mode fiber. Depending on the desired CRDS cavity requirements, this will allow the cavity to support either a single or multiple modes. For example, if the optical signal has a narrow bandwidth, comprised of only one wavelength, then a single mode fiber optic is needed. However, to support an optical signal of varying wavelengths and colors, a large, multimode fiber optic is needed.

A fiber-coupling lens is shown in FIG. 3 at 301 and 308, and is used to guide the optical signal into the length of optical fiber at 307 and 305, respectively, Additional fiber coupling lenses can be used to enhance the coupling efficiency of the light into the fiber.

Figure 5:
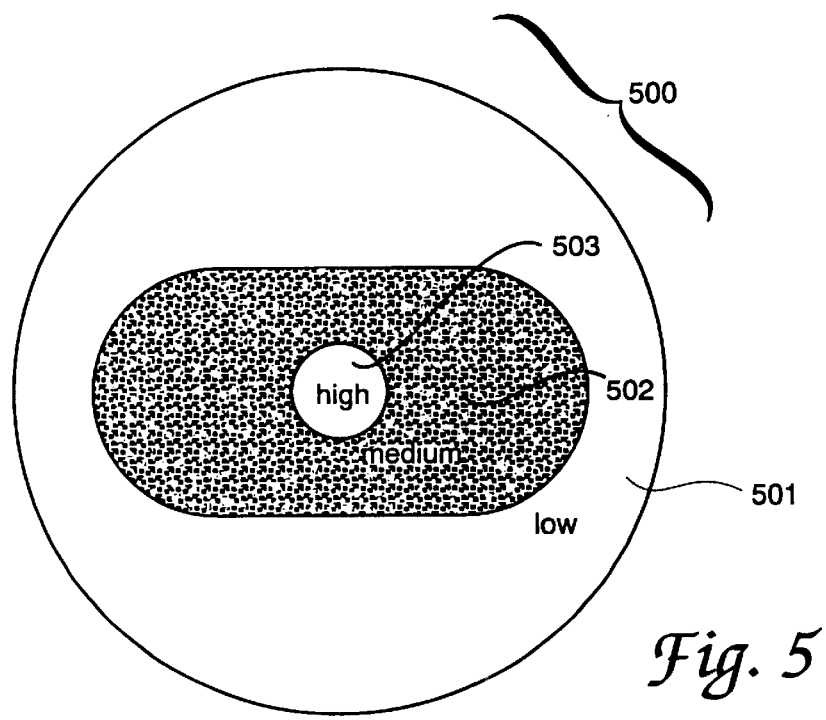
FIG. 5 shows a cross-sectional view of a fiber amplifier active section according to the invention.

The fiber amplifier active section 303 is contained within the length of optical fiber. The fiber amplifier active section is capable of increasing coherent photon count of said optical signal. A schematic of such an optical fiber active section or optical fiber amplifier is shown in FIG. 5. In the arrangement of FIG. 5, the fiber amplifier is a double-clad optical fiber, which has been doped with a rare-earth lasing material and is pumped with a high power diode laser. Regions of low, medium and high index of refraction are shown at 501, 502 and 503, respectively. Most commonly used optical fibers have only high and low index regions. A double-clad optical fiber is used in the arrangement of the present invention because it allows for an incoherent (multimode) pump source to be coupled into the multimode medium index region 502 and subsequently for optical power to be transferred to the single mode high index region 503.

Pumping the optical fiber with a high power diode laser is significant because it increases the photon count within the optical fiber active section operating as an amplifier. The optical signal enters the active region, shown at 303 in FIG. 3, and the photon count or energy of the optical signal is increased as it exits the active region 303 with a greater optical intensity than when it entered.

The gain of the fiber amplifier is modulated between two levels. The first level, in which the gain of the fiber amplifier will be greatest, will allow for a round trip gain of greater than unity and build up of light inside the cavity. Once a sufficient amount of light is circulating in the cavity, the gain of the fiber amplifier will be reduced to a lower level appropriate to produce a transparent cavity in the absence of absorbing species. The appropriate level can be predetermined by performing application specific tests specific to the system to determine appropriate gain. In other words, the second gain level will result in an infinite cavity ring-down time constant for an empty cavity. The introduction of absorbing species will result in the loss of this transparency condition and finite ring-down decay time constants, useful for characterizing absolute concentrations of absorbing species.

The wavelength of the laser light produced by the fiber amplifier can be varied by controlling either the temperature in the fiber amplifier active section or by controlling the amplifier current in the fiber amplifier active section. The fiber amplifier temperature or current amplitude can be preselected and the fiber amplifier can be initialized accordingly.

A significant aspect of this design is that both orthogonal polarizations of light can be utilized in the CRDS cavity. Every optical signal is composed of light polarized in either of two polarizations or dimensions, a perpendicular and a parallel polarization. Both polarizations of light can be utilized in this arrangement as they are used in other CRDS experiments. A polarizing beam splitter can be utilized to separate the orthogonal polarizations for measurement and control.

Figure 4:
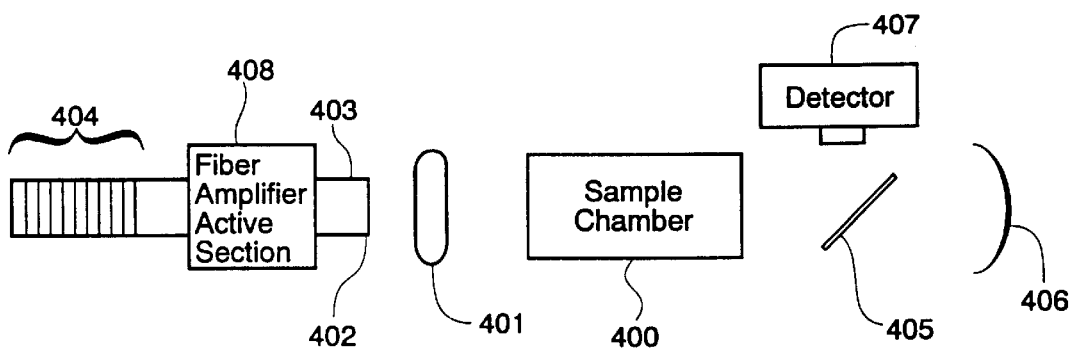
FIG. 4 shows a schematic diagram of a CRDS system using a fiber amplifier and Bragg reflection grating according to the invention.

A second possible arrangement of the invention is shown in FIG. 4. FIG. 4 consists of a sample chamber 400 with a concave mirror 406 at one end and a length of optical fiber 403 with a Bragg reflection grating 404 written inside the fiber at the other end. A fiber amplifier active section 408 is contained within the length of optical fiber.

In the operation of this arrangement, an optical signal is generated in the active optical fiber and is transmitted to the sample chamber 400. The signal then begins resonating and a beamsplitter 405 transmits a sample of the optical signal to detector 407. The signal is then reflected off the concave mirror at 406, transmitted through the sample chamber again and through fiber coupling lens 401 into the optical fiber 403 at the opening 402. In the arrangement of FIG. 4, additional fiber coupling lenses may be used to increase coupling efficiency.

As in the arrangement of FIG. 3, the fiber amplifier active section 408 produces an optical signal gain compensating for system losses. The Bragg reflection grating 404 receives the optical signal from the fiber amplifier active section 408 and reflects the signal back. Generally, a Bragg reflection grating contains periodically varying indices of refraction written within the length of optical fiber. These regions of periodically varying index of refraction are designed so that the phase relationship between reflections of subsequent regions sums to produce constructive interference and strong reflections at particular wavelengths. It is possible to tune the peak reflection wavelength over a small range through temperature tuning. In the arrangement of the invention, the Bragg reflection grating 404 operates like a wavelength specific high reflection mirror. The optical signal resonates or "rings down" between the optical mirror 406 and the Bragg reflection grating 404 with loss compensating gain achieved at the fiber amplifier active section 408. The arrangement is therefore useful for samples with high absorption coefficients.

Alternatively, the optical mirror 406 could be replaced with a length of optical fiber containing another Bragg reflection grating, making the arrangement insensitive to optical misalignment and capable of portability.

The present invention provides an improved capability cavity ring down spectroscopy (CRDS) system and makes it suitable for samples with high absorption coefficients. The present invention uses the optical gain available in a fiber amplifier to compensate for all system optical losses commonly seen in conventional CRDS systems, including those due to fiber coupling and light detection. Additionally the present invention provides a CRDS system that is immune to cavity misalignment and therefore inminently capable of portability.

While the apparatus and method herein described constitute a preferred embodiment of the invention, it is to be understood that the invention is not limited to this precise form of apparatus or method and that changes may be made therein without departing from the scope of the invention which is defined in the appended claims.

I claim:

1. An optical loss system misalignment minimizing cavity ring down spectroscope for measuring absolute concentrations of absorbing species comprising:
   an optical signal source;
   a sample chamber;
   an optical signal splitter, separating said optical signal and directing a sample to an optical photodetector;
   a length of optical fiber receiving said optical signal from said optical signal receiving absorbing species sample chamber and transmitting said optical signal therethrough;
   an optical signal loss compensating fiber amplifier active section within said length of optical fiber; and
   a lens coupling said optical signal from said optical signal loss compensating fiber amplifier into said optical signal receiving absorbing species sample chamber.

2. The optical loss system misalignment minimizing cavity ring down spectroscope for measuring absolute concentrations of absorbing species of claim 1 wherein said optical signal loss compensating fiber amplifier further comprises amplifying material increasing coherent photon count of said optical signal.

3. The optical loss system misalignment minimizing cavity ring down spectroscope for measuring absolute concentrations of absorbing species of claim 1 wherein said optical signal loss compensating fiber amplifier active section further comprises optical signal wavelength control means.

4. The optical loss system misalignment minimizing cavity ring down spectroscope for measuring absolute concentrations of absorbing species of claim 3 wherein said optical signal wavelength control means comprises fiber amplifier active section temperature control means.

5. The optical loss system misalignment minimizing cavity ring down spectroscope for measuring absolute concentrations of absorbing species of claim 3 wherein said optical signal wavelength control means comprises fiber amplifier active section-amplifier current control means.

6. The optical loss system misalignment mining cavity ring down spectroscope for measuring absolute concentrations of absorbing species of claim 1 wherein said optical signal loss compensating fiber amplifier is a double-clad fiber optic cable having a rare earth doped component and wherein said double-clad fiber optic cable is pumped with a diode laser.

7. The optical loss system misalignment minimizing cavity ring down spectroscope for measuring absolute concentrations of absorbing species of claim 1 wherein said optical fiber has an anti-reflection coating.

8. The optical loss system misalignment minimizing cavity ring down spectroscope for measuring absolute concentrations of absorbing species of claim 1 wherein said optical signal loss compensating fiber amplifier within said length of optical fiber is a gain modulating fiber amplifier, said gain modulated between two levels.

9. The optical loss system misalignment minimizing cavity ring down spectroscope for measuring absolute concentrations of absorbing species of claim 1 wherein said sample chamber has first and second opposing ends.

10. The optical loss system misalignment minimizing cavity ring down spectroscope for measuring absolute concentrations of absorbing species of claim 1 wherein said length of optical fiber communicates with both first and second opposing ends of said sample chamber.

11. The optical loss system misalignment minimizing cavity ring down spectroscope for measuring absolute concentrations of absorbing species of claim 1 wherein said optical signal source is said optical signal loss compensating fiber amplifier active section.

12. An optical loss system misalignment minimizing cavity ring down spectroscope for measuring absolute concentrations of absorbing species comprising:
   an optical signal source;
   a sample chamber;
   a directional optical signal splitter, splitting said optical signal and directing a small portion of said optical signal to an optical photodetector;
   a length of optical fiber receiving said directional optical signal, optical signal losses resulting from transmission of said directional optical signal;
   an optical signal loss compensating fiber amplifier active section within said length of optical fiber, a wavelength specific, highly reflective Bragg reflection grating within said length of optical fiber; and
   a lens coupling said directional optical signal from said optical signal loss compensating fiber amplifier active section into said sample chamber.

13. The optical loss system misalignment minimizing cavity ring down spectroscope for measuring absolute concentrations of absorbing species of claim 12 wherein said optical signal loss compensating fiber amplifier comprises coils increasing coherent photon count of said optical signal.

14. The optical loss system misalignment minimizing cavity ring down spectroscope for measuring absolute concentrations of absorbing species of claim 12 wherein said optical fiber has an anti-reflection coating.

15. The optical loss, system misalignment minimizing cavity ring down spectroscope for measuring absolute concentrations of absorbing species of claim 12 wherein said optical signal source is said optical signal loss compensating fiber amplifier active section.

16. An optical loss system misalignment minimizing cavity ring down spectroscopy method for measuring absolute concentrations of absorbing species comprising the steps of:
   providing an optical signal source;
   receiving said optical signal into a sample chamber;
   splitting said optical signal and directing a portion of said optical signal to an optical photodetector;
   transmitting said optical signal from said sample chamber through a length of optical fiber, optical signal losses resulting from said transmitting;
   amplifying said optical signal traveling through said length of optical fiber, said amplifying compensating for said optical signal losses;
   retransmitting said optical signal from said amplifying step into said sample chamber; and
   repeating said amplifying and retransmitting steps until the optical signal rings down.

17. The optical loss system misalignment minimizing cavity ring down spectroscopy method for measuring absolute concentrations of absorbing species of claim 16 for measuring absolute concentrations of absorbing species wherein said amplifying step further comprises the step of transmitting said optical signal through a fiber amplifier within said length of optical fiber.

18. The optical loss system misalignment minimizing cavity ring down spectroscopy method for measuring absolute concentrations of absorbing species of claim 17 wherein said step of transmitting further comprises transmitting said optical signal through an optical signal loss compensating fiber amplifier with a double-clad fiber optic cable having a rare earth doped component and wherein said double-clad fiber optic cable is pumped with a diode laser.

19. The optical loss system misalignment minimizing cavity ring down spectroscopy method for measuring absolute concentrations of absorbing species of claim 16 wherein said amplifying step further comprises the step of providing amplifying material for transmitting said optical signal therethrough, said amplifying material increasing coherent photon count of said optical signal.

* * * * *

UNITED STATES PATENT AND TRADEMARK OFFICE
CERTIFICATE OF CORRECTION

PATENT NO. : 6,532,072 B1
DATED : March 11, 2003
INVENTOR(S) : Craig C. Largent

It is certified that error appears in the above-identified patent and that said Letters Patent is hereby corrected as shown below:

Column 6,
Line 52, "section-amplifier" should read -- section amplifier --.
Line 53, "mining" should read -- minimizing --.

Column 7,
Line 30, "a wavelength" should begin a new paragraph.

Signed and Sealed this

Fifteenth Day of July, 2003

JAMES E. ROGAN
*Director of the United States Patent and Trademark Office*